United States Patent [19]
Vassiliadis et al.

[11] Patent Number: 5,207,576
[45] Date of Patent: May 4, 1993

[54] DENTAL LASER ASSEMBLY WITH DUAL LASERS

[75] Inventors: Arthur Vassiliadis, Mountain View; David R. Hennings, Newcastle; Joseph W. Shaffer, Mountain View, all of Calif.; Terry D. Myers, Farmington Hills, Mich.

[73] Assignee: American Dental Laser, Inc., Troy, Mich.

[21] Appl. No.: 343,401

[22] Filed: Apr. 25, 1989

Related U.S. Application Data

[63] Continuation-in-part of Ser. No. 335,215, Apr. 7, 1989, abandoned.

[51] Int. Cl.⁵ .................. A61C 5/00; A61B 17/36
[52] U.S. Cl. .................................. 433/215; 606/15; 606/18
[58] Field of Search .................. 433/215, 229; 128/303.1, 397, 398

[56] References Cited

U.S. PATENT DOCUMENTS

| | | | |
|---|---|---|---|
| 4,408,602 | 10/1983 | Nakajima | 606/18 |
| 4,521,194 | 6/1985 | Myers et al. | 433/215 |
| 4,672,961 | 6/1987 | Davies | 128/398 X |
| 4,784,135 | 11/1988 | Blum et al. | 128/395 X |

FOREIGN PATENT DOCUMENTS

| | | | |
|---|---|---|---|
| 0253734 | 1/1988 | European Pat. Off. | 128/303.1 |
| 0284330 | 9/1988 | European Pat. Off. | 128/303.1 |
| 8501870 | 5/1985 | World Int. Prop. O. | 128/303.1 |
| 8704632 | 8/1987 | World Int. Prop. O. | 128/303.1 |

Primary Examiner—Gene Mancene
Assistant Examiner—Nicholas D. Lucchesi
Attorney, Agent, or Firm—Gifford, Groh, Sprinkle, Patmore and Anderson

[57] ABSTRACT

A dental laser assembly having a housing with a first and second laser cavity. The housing also includes an optical output port and a dental optical delivery system optically connected to the port. A first laser is contained within a first laser cavity which, when activated, generates a first laser beam while, similarly, a second laser is contained within a second laser cavity which, when activated, generates a second laser beam. Only one laser, however, is activated at a given time and the output beam from the activated laser is directed to the optical output port in the housing for use in dental applications. The first laser has optical qualities sufficient to perform a first set of dental procedures while the second laser has optical qualities sufficient to perform a second and different set of dental procedures.

11 Claims, 1 Drawing Sheet

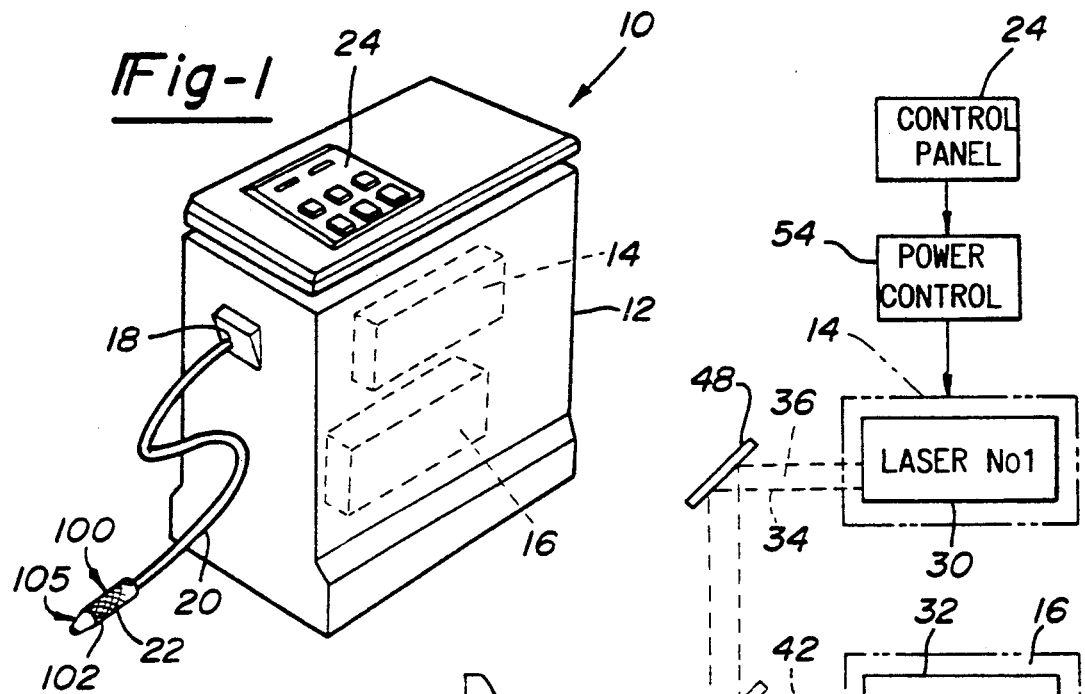

DENTAL LASER ASSEMBLY WITH DUAL LASERS

CROSS REFERENCE TO RELATED APPLICATIONS

This application is a continuation-in-part of U.S. patent application Ser. No. 335,215, entitled DENTAL LASER ASSEMBLY WITH DUAL LASERS, filed on Apr. 7, 1989, now abandoned.

BACKGROUND OF THE INVENTION

I. Field of the Invention

The present invention relates generally to medical laser systems and, more particularly, to a dental laser assembly having two lasers for use in different dental applications.

II. Description of the Prior Art

There are numerous previously known lasers which have been used in a number of different medical applications. For example, a YAG laser has been previously used in cataract surgery for opening opacified lenses or capsules in the eye. Similarly, other lasers have been used in various surgical applications, such as brain surgery.

The use of lasers in dentistry is a presently evolving field in which the inventors are intimately involved. Dental applications using lasers include not only the removal of incipient carious lesions and/or stains on the outer surface of the tooth, but also the removal of dentin, enamel as well as diseased mouth tissue. This diseased mouth tissue includes, for example, diseased gum tissue as well as diseased nerve tissue in endontic procedures.

It has been found that lasers having different optical qualities are best suited for different medical applications. For example, YAG lasers having certain energy levels, pulse durations, wave lengths and the like are used in cataract surgery Conversely, continuous wave $CO_2$ lasers having different wave lengths and different power levels are used in different types of medical applications, such as surgical applications. Furthermore, the use of a $CO_2$ continuous laser would be completely inappropriate for use in cataract surgery and, similarly, a YAG laser is not as effective for use in certain surgical medical procedures.

Consequently, it has been the previous practice to design a separate and independent laser for each type of medical procedure desired. This practice, however, disadvantageously increases the overall cost of medical equipment when two or more lasers are necessary in order to perform different medical procedures. In addition, if a complex procedure requires two different lasers for sequential steps in the procedure, the convenience of not having to move two laser systems would be valuable.

For example, one type of laser having certain optical qualities is sufficient for certain medical procedures, such as removing incipient carious lesions and/or stain from the surface of teeth. Conversely, a laser having different optical qualities is necessary in order to perform other medical procedures, such as eradicating enamel and dentin. For soft gum tissue as well as diseased nerve tissue in endontic applications, one or the other of the lasers may be appropriate. Consequently, in order for a dental office to be fully laser equipped, it would be necessary to have two independent lasers, one laser for certain procedures and a separate laser for other procedures.

SUMMARY OF THE PRESENT INVENTION

The present invention provides a dental laser assembly which overcomes the above mentioned disadvantages.

In brief, the dental laser assembly of the present invention comprises a housing having a first laser cavity and a second laser cavity. The housing also includes an optical output port as well as a dental optical delivery system which is adapted for connection to the port.

A first laser is contained within the first optical cavity which, when activated, generates a first laser beam. Furthermore, this laser beam has optical qualities capable of performing a first set of dental procedures, such as removing incipient carious lesions and/or stain from the surface of teeth, and the desensitization of teeth.

A second laser is contained within the second laser cavity which, when activated, generates a second laser beam. This second laser beam has optical qualities capable of performing a second set of dental procedures, such as eradicating enamel, dentin, diseased soft gum tissue and diseased nerve tissue in endontic applications.

The first and second sets of dental procedures are substantially mutually exclusive from each other, although there may be some overlap.

The present invention also includes means for selectively activating only one of the two lasers at a given time as well as means for directing the laser beam from the activated laser to the optical port. In one embodiment of the invention, a movable mirror is contained within the housing and movable between a first and second position. In its first position, the mirror reflects the laser beam from the first laser to the optical port while, conversely, in its second position, the mirror allows the laser beam from the second laser to reach the optical port.

In a second embodiment of the invention, a dichroic beam splitter is positioned in the housing so that both laser beams, when activated, impinge upon the beam splitter. The beam splitter directs the first or second laser beam, depending upon which laser is activated, to the optical port in the desired fashion.

A primary advantage of Applicants' invention is that a number of the components in the dental laser assembly are utilized regardless of which of the two lasers is activated. For example, a common power supply, a common optical delivery system, a single enclosure, a single control panel, a single microprocessor and controller, and a single focusing lens are employed regardless of which laser is activated. Consequently, the only additional cost of the dual laser systems, as opposed to a single laser system is the cost of (1) the second laser and (2) the means for selectively directing the beam output from the activated laser towards the optical output port.

A unique dental handpiece particularly suited for cutting soft gum and mouth tissue is also disclosed.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which:

FIG. 1 is a view illustrating a preferred embodiment of the present invention;

FIG. 2 is a diagrammatic view illustrating a preferred embodiment of the present invention;

FIG. 3 is a view similar to FIG. 2, but illustrating a second preferred embodiment of the present invention; and FIG. 4 is a fragmentary sectional view illustrating one component of the preferred embodiment of the present invention.

DETAILED DESCRIPTION OF PREFERRED EMBODIMENTS OF THE PRESENT INVENTION

With reference first to FIG. 1, a preferred embodiment of the dental laser assembly 10 of the present invention is thereshown and comprises a housing 12 having a first laser cavity 14 and a second laser cavity 16. These cavities 14 and 16 will be subsequently described in greater detail.

Still referring to FIG. 1, an optical output port 18 is also provided on the housing 12. An optical delivery system 20, such as a fiber optic cable, is attachable to the optical port 18 in any conventional fashion. A handpiece 22 is attached to the distal or free end of the optical cable 20 and is particularly designed for use in dental applications. These dental applications will be subsequently described.

A control panel 24 is mounted on the housing 12 which controls the activation of the dental laser assembly 10. The control panel 24 preferably includes a touch pad which is conventional in construction so that a further description thereof is unnecessary.

Referring now to FIG. 2, a first laser 30 is contained within the first laser cavity 14 while, similarly, a second laser 32 is contained within the second laser cavity 16. The first laser 14, when activated, produces a first laser beam 34 along a predetermined axis 36. Similarly, the second laser 32, when activated, generates a second laser beam 40 along a predetermined axis 42.

Still referring to FIG. 2, a mirror 46 is movable between a first position illustrated in phantom line and a second position illustrated in solid line. Any conventional means, such as a solenoid 49, can be used to move the mirror 46 between its first and second positions.

With the mirror 46 in its first position (phantom line) the mirror 46 is aligned with the axis 42 of the second laser output beam 40 and is angled substantially 45° with respect to the axis 42. A stationary mirror 48 is aligned with the laser beam 34 from the first laser 30 so that the laser beam 34 is reflected by a stationary mirror 48 to the movable mirror 46 and, by the movable mirror 46, along a laser output path 50. The output path 50 passes through a focusing mirror 52 to the housing optical output port 18. Consequently, with the mirror 46 in its first position (phantom line) and assuming that the first laser 30 is activated, the output beam 34 from the first laser 30 is directed to the output port 18 in the above described fashion. Furthermore, during this time, the second laser 32 is not activated.

Conversely, with the mirror 46 moved to its second position (solid line) and upon activation of the second laser 32, the laser beam 40 from the second laser 32 follows the laser output path 50 through the focusing lens 52 and to the optical output port 18. At this time, furthermore, only the second laser 32 and not the first laser 30 is activated.

Consequently, by moving the mirror 46 between its first and second position, and by selectively activating only the first laser 30 or the second laser 32, depending upon the position of the mirror 46, either the output beam 34 from the first laser, or the output beam 40 from the second laser is directed to, i.e. optically connected with, the output port 18. Appropriate control circuitry 54 controls not only the activation of the lasers 30 and 32, but also the activation of the solenoid 49 in order to properly position the mirror 46 as desired.

With reference now to FIG. 3, a second preferred embodiment is shown in which a dichroic beam splitter 60 replaces the mirror 46 and is positioned in the same general location as the first position of the mirror 46. Consequently, upon activation of the first laser 30, the stationary mirror 48 and beam splitter 60 reflect the output beam 34 along the output path 50 to the optical output port 18 as desired. Conversely, upon activation of the second laser 32, the output beam 40 passes through the dichroic beam splitter 60, along the output path 50 and to the output port 18 in the desired fashion.

The control panel 24 and the associated power and control circuitry 54 are used in common for both the first laser 30 and the second laser 32. Consequently, the only additional components necessary to achieve laser output from either the first laser 30 or the second laser 32 is the laser itself as well as the associated mirrors 48 and 46 and/or the beam splitter 60. Otherwise, the power supply, power circuitry, control circuitry and the like are used for both the first and second laser since only one of the lasers 30 and 32 are activated at a single time.

The lasers 30 and 32 are designed for different dental applications. More specifically, the first laser 30 has optical qualities sufficient to perform a first set of dental procedures while the second laser 32 has optical qualities sufficient to perform a second set of dental procedures. The first and second sets are substantially mutually exclusive of each other although there may be some overlap.

For example, the first set of dental procedures includes the eradication of carious lesions, stains on the outer surface of the tooth, tooth desensitization and some soft tissue applications. Such stains and/or lesions have not yet invaded the dentin.

The optical qualities of the first laser necessary to accomplish these dental procedures are a laser having a wave length of between 0.2 and 2.0 micrometers, a pulse duration of between several picoseconds and several milliseconds, an energy level of between 0.1 millijoules and 5 joules, a beam diameter in the range of 10 to 5000 microns and a pulse repetition rate of between 1 pulse per second to 10,000 pulses per second.

The second set of dental procedures includes the eradication of enamel, dentin, diseased soft gum tissue as well as diseased nerve tissue in endontic procedures, such as root canals. The second laser thus has a wave length of between 2.0 and 5.0 micrometers, a beam diameter in the range of 10–5000 microns, a pulse duration of between several picoseconds and several milliseconds, an energy level of between 0.1 millijoules and 5 joules per pulse and a pulse repetition rate of between 1 pulse per second to 10,000 pulses per second. In practice, a laser having these optical qualities is sufficient to perform these dental procedures in the second set.

Referring now to FIGS. 1 and 4, one of the many possible designs of a dental handpiece 100 for the laser system is thereshown and comprises an elongated body 102 having a longitudinal throughbore 104. An end 105 of the optical fiber 20 is positioned in the bore 104.

A conical tip 105 fits on the free end of the handpiece body 102. The tip 105, which is particularly useful for cutting soft mouth tissue, such as gum tissue, is made of a material that transmits, i.e. is transparent to, the laser radiation, such as quartz, or other material. The distal end of the tip 105 is treated by a coating method, or other process, by a very thin layer 108 of an absorbing material, such as carbon, or other material. The effect of this thin coating 108 is that it can reach a very high temperature in a very short time, when the laser is fired, and thus provides a cutting action on tissues, and then rapidly cools off when the laser is turned off. Many other designs of handpieces can be used including one similar to the above, but without a coating.

From the foregoing, it can be seen that the present invention provides a dual laser system for dental applications for performing different dental procedures which overcomes the previously mentioned disadvantages of the previously practices.

Having described our invention, however, many modifications thereto will become apparent to those skilled in the art to which it pertains without deviation from the spirit of the invention as defined by the scope of the appended claims.

We claim:

1. A dental laser comprising:
    a housing having a first laser cavity and a second laser cavity,
    said housing having at least one optical output port,
    a dental optical delivery system connected to said port,
    a first laser contained in said first cavity which, when activated, generates a first laser beam,
    a second laser contained in said second laser cavity which, when activated, generates a second laser beam,
    means for selectively activating only one of said lasers at a given time, and
    means for directing the laser beam from the activated laser to said at least one port,
    wherein said first laser beam has optical qualities sufficient to perform any of a first set of dental treatment therapeutic procedures in a mouth,
    wherein said second laser beam has optical qualities sufficient to perform any of a second set of dental treatment therapeutic procedures in a mouth,
    wherein said first set of dental treatment procedures is substantially mutually exclusive from said second set of dental procedures,
    wherein said first laser is a pulse laser and has a wave length of between 0.2 and 2.0 micrometers, a beam diameter at a target site of 10–5000 microns and a pulse duration of between several picoseconds and several milliseconds, and an energy of between 0.1 millijoules and 1 joules per pulse,
    wherein said second laser is a pulse laser and has a wave length of 2.0 to 5.0 micrometers, a beam diameter of 10 to 5000 microns at a target site, a pulse duration of several picoseconds to several milliseconds, and an energy of 0.1 millijoules to 5 joules per pulse.

2. The invention as defined in claim 1 wherein said directing means comprises a mirror movable between a first position and a second position wherein in said first position, said mirror reflects said first laser beam to said port, wherein in said second position said mirror enables said second laser beam to impinge upon said port.

3. The invention as defined in claim 2 wherein said mirror is angled substantially 45° with respect to an axis of said second laser beam, means for directing said first laser beam substantially perpendicularly with respect to said second laser beam and so that said first laser beam impinges upon said mirror, wherein in said first position said mirror is positioned along said axis of said second laser beam and wherein in said second position said mirror is laterally spaced from the axis of said second laser beam.

4. The invention as defined in claim 1 wherein said directing means comprises a dichroic beam splitter positioned in the path of both of said laser beams.

5. The invention as defined in claim 1 wherein said first set of dental procedures includes the removal of incipient carious lesions from teeth and wherein the second set of dental procedures includes the removal of tooth decay which has invaded the dentin.

6. The invention as defined in claim 5 wherein said second set of dental procedures includes the removal of soft tissue contained in the mouth.

7. The invention as defined in claim 5 wherein said second set of dental procedures includes endontic dental procedures.

8. The invention as defined in claim 7 wherein said endontic procedures includes a root canal dental procedure.

9. The invention as defined in claim 5 wherein said first set of dental procedures includes desensitization of teeth.

10. The invention as defined in claim 5 wherein said second set of dental procedures includes the sterilization of soft mouth tissue.

11. The invention as defined in claim 5 wherein said second set of dental procedures includes eradicating enamel.

* * * * *